United States Patent
Maione et al.

(10) Patent No.: US 10,444,173 B2
(45) Date of Patent: Oct. 15, 2019

(54) METHOD AND SYSTEM OF THERMOGRAPHIC NON-DESTRUCTIVE INSPECTION FOR DETECTING AND MEASURING VOLUMETRIC DEFECTS IN COMPOSITE MATERIAL STRUCTURES

(71) Applicant: Leonardo S.p.A., Rome (IT)

(72) Inventors: Giacomo Maione, Rome (IT); Ciro Incarnato, Rome (IT); Antonio Ciliberto, Rome (IT); Umberto Galietti, Rome (IT); Davide Palumbo, Rome (IT); Gianpiero Cerrone, Rome (IT)

( * ) Notice: Subject to any disclaimer, the term of this patent is extended or adjusted under 35 U.S.C. 154(b) by 507 days.

(21) Appl. No.: 15/216,221

(22) Filed: Jul. 21, 2016

(65) Prior Publication Data

US 2017/0023505 A1   Jan. 26, 2017

(30) Foreign Application Priority Data

Jul. 22, 2015 (IT) .................. 102015000037077

(51) Int. Cl.
*G01B 21/22* (2006.01)
*G01D 5/00* (2006.01)
(Continued)

(52) U.S. Cl.
CPC ............. *G01N 25/72* (2013.01); *G01B 21/18* (2013.01); *G01J 5/10* (2013.01); *G01M 5/0033* (2013.01);
(Continued)

(58) Field of Classification Search
CPC .... G01B 21/18; G01J 5/10; G01J 2500/0077; G01J 2005/0081; G01M 99/002; G01N 25/72
See application file for complete search history.

(56) References Cited

U.S. PATENT DOCUMENTS

2004/0041096 A1   3/2004   Sun et al.

FOREIGN PATENT DOCUMENTS

DE          19907804 C1      3/2000
DE       102012003813 A1     8/2013
(Continued)

OTHER PUBLICATIONS

Italian Ministry of Economic Development, Search Report and Written Opinion for IT UB20152385, dated Mar. 31, 2016.
(Continued)

*Primary Examiner* — Sujoy K Kundu
*Assistant Examiner* — L. Anderson
(74) *Attorney, Agent, or Firm* — Greer, Burns & Crain, Ltd.

(57) ABSTRACT

A thermographic non-destructive inspection method of a structure, comprising the steps of: generating a modulated thermal wave in the direction of the structure; generating a temperature signal identifying a phase shift between the modulated thermal wave and a return thermal wave emitted from the structure; processing the temperature signal to obtain a first sub-signal related to the phase of the first harmonic of the temperature signal; identifying a first dimension of said defect as a function of the phase of the first harmonic of the temperature signal; calculating a first and a second intermediate parameter by calculating the difference between the phase value inside the zone with a defect and the phase value, absolute or mean of a plurality of points, of the undamaged zone close to the defect; and identifying a second dimension of the defect as a function of the first dimension and of the intermediate parameters.

16 Claims, 5 Drawing Sheets

(51) Int. Cl.
    *G01N 25/72* (2006.01)
    *G01M 5/00* (2006.01)
    *G01M 99/00* (2011.01)
    *G01B 21/18* (2006.01)
    *G01J 5/10* (2006.01)
    *G01J 5/00* (2006.01)

(52) U.S. Cl.
    CPC ... *G01M 99/002* (2013.01); *G01J 2005/0077* (2013.01); *G01J 2005/0081* (2013.01)

(56) References Cited

FOREIGN PATENT DOCUMENTS

| | | |
|---|---|---|
| WO | WO02089042 A1 | 11/2002 |
| WO | WO2014044986 A2 | 3/2014 |

OTHER PUBLICATIONS

Celorrio, R. et. al. "Vertical cracks characterization using lock-in thermography: II finite cracks", Measurement Science and Technology, Sep. 22, 2014, p. 115602, vol. 25, No. 11, IOP, Bristol, GB.

Dorr, Peter, el al. "Multi-parameter-fitting procedure for photothermal infrared radiometry on multilayered and bulk-absorbing solids", Journal of Applied Physics, Jun. 15, 2011, pp. 7888-7894, vol. 89, No. 12, American Institute of Physics, US.

Streza, M., et. al. "Heat transfer modeling for surface crack depth evaluation", Measurement Science and Technology, Mar. 7, 2013, p. 45602, vol. 24, No. 4, IOP, Bristol, GB.

METHOD AND SYSTEM OF THERMOGRAPHIC NON-DESTRUCTIVE INSPECTION FOR DETECTING AND MEASURING VOLUMETRIC DEFECTS IN COMPOSITE MATERIAL STRUCTURES

The present invention relates to a thermographic non-destructive inspection method and system for detecting and measuring defects of a volumetric type, such as, for example, resin pockets in composite material structures.

BACKGROUND OF THE INVENTION

As is known, during the manufacture of laminar composite material structures, for example in carbon, a resin matrix is used to keep the fibres in place and give shape to the manufactured composite article. In this context, the formation of undesired pockets, or accumulations, of resin that would compromise the stress resistance of the article manufactured in this manner are sometimes observed. The formation process of resin pockets is the following (other types of pocket originate in a similar manner): when layers of composite material deform (orthogonally to the lamination plane) during manufacture, empty spaces or anomalous pressure conditions may generate. In particular, during the polymerization phase, resin in the liquid phase can fill these spaces, thus creating resin canals, or build-ups of resin, known as resin pockets, (parallel to the generatrix of the curved segment in the case of radial parts), which follow the profile of the first layer affected by the deformation. In some cases, the pockets can be filled by a material other than resin (adhesive, sealant, etc.).

The presence of the aforesaid resin pockets produces a wrinkling condition in which wrinkles can be formed both in the flat laminates and in curved zones (such as, for example, sections having a C, T, L, I or J shape). Non-destructive thermal, or thermographic, inspection methods for detecting these aforementioned defects, for example lock-in thermography, are known in the state of the art and used for detecting defects in a generic item or body under analysis. In fact, during heat stimulation, the defect in the body being tested reaches a different temperature from that reached by the surrounding material and/or the same temperature at different times (and which does not exhibit defects). This behaviour is due to the different thermo-physical properties involved in the heat-transmission phenomena, for example, the thermal conductivity of the material, the density of the material, etc.

In fact, if the item is opportunely stimulated, by means of suitable lamps, the presence of a defect creates a change in the normal heat diffusion, causing local lack of uniformity in surface temperature distribution on the item under investigation, easily identifiable through the use of a thermographic camera.

Thermographic technology is based on detecting the infrared radiation emitted from the body being tested, and exploits opportune sensors that work without having to be in contact with the body, determining the temperature and generating a thermal image.

The thermal image provided represents a map of the temperature distribution in the body being tested, from which it is possible to extract information regarding the internal structure of the body. The applications of thermographic technology cover the most varied sectors: from energy to infrastructure, from the transport and aeronautics industries to the conservation of cultural heritage and the medical industry. In the aeronautics field, thermography can be used as a non-destructive method for the periodic inspection of parts, to detect any defects that might arise during an aircraft's working life, or during the design and assembly stages.

The use of thermography in the non-destructive inspection sector is in rapid growth, linked to the considerable advantages this technology offers. Thermal maps can be obtained quickly and enable inspecting large surfaces without any contact with the structures being tested. This advantage results in a significant reduction in machine downtime, as no disassembly is necessary in order to perform the thermographic analysis. Lock-in thermography is applicable to the inspection of composite materials, for example carbon fibres, for which many classical technologies cannot be used.

On the other hand, traditional thermography is affected by some limits due to disturbances, such as non-uniform heating, reflections from heat sources in the working environment and non-homogeneous emissivity coefficients, which could be reproduced on the image of the item being tested and could therefore prejudice the result of the inspection.

For this reason, the processing of the acquired thermal signal currently represents an important field of investigation and study, for the purpose of identifying and separating the useful signal from the noise.

In lock-in thermography, temperature modulation induced by the heating system has a sinusoidal or square waveform, and propagates like a "thermal wave" inside the body being tested. This wave undergoes a series of reflections inside the body, such that the temperature modulation at the surface of the body is a function of the thermal wave that "returns" from inside the body.

The amplitude image of the wave reflected by the body is dependent on the surface's non-uniform absorption, infrared emission and the heating distribution, while the phase image is not particularly affected by these disturbances, generally resulting more reliable and sensitive. Furthermore, through phase analysis, the theoretical depth at which a defect ($\mu$) can be detected is approximately twice that achievable with amplitude analysis and depends on the following formula:

$$\mu = \sqrt{\frac{2k}{\omega \rho C_p}} = \sqrt{\frac{2\alpha}{\omega}}$$

where: k is the heat conductivity of the material, $\omega$ is the angular velocity (equal to 2nf, where f is the frequency of the emitted sinusoidal wave), $\rho$ is the density, and $C_p$ is the thermal capacity. The constant $\alpha$ represents the thermal diffusivity.

The emitted thermal wave can be obtained in various ways. For example, as shown in FIG. 1, one or more halogen lamps 3 connected to a signal generator 5 designed to generate a control signal (on/off) for the halogen lamps 3 variable in amplitude and frequency (for example, according to a sinusoidal or square waveform) could be used. In this way, one or more halogen lamps 3 generate, in use a modulated thermal wave, for example with square or sinusoidal wave modulation. Even more specifically, this modulated signal has a period of 25 seconds in this particular application.

A thermographic camera 8 acquires the thermal image of the item 4 being tested and sends the acquired data to a computer 7. The computer 7 acquires the signals coming from both the thermographic camera 8 and the trigger of the signal generator 5, which regulates the on/off phases of the halogen lamp 3. Specially provided software, stored in a memory of the computer 7, processes the data received by the computer 7 to generate phase and/or amplitude images of the thermal wave emitted from the body being tested.

Document WO 2014/044986 related to a method for assessing the depth of a crack in un metal material (a defect of the "vertical crack" type, also known in the state of the art as a "planar defect"). These defects are characterized by a vertical extension that is much larger than the extension in width, which is hence ignored (for this reason, the defect is considered two-dimensional). The method divulged in that document does not allow thermographic inspection for "volumetric" defects (i.e. defects where none of length, width and depth can be overlooked), as are resin pockets that occur in composite material structures, for example in glass fibre or carbon fibre.

SUMMARY OF THE INVENTION

The object of the present invention is to provide a thermographic non-destructive inspection method and system for detecting and measuring defects of a volumetric type, especially in composite material structures, such as to overcome the drawbacks of the known art.

According to the present invention, a thermographic non-destructive inspection method and system are provided for detecting and measuring a volumetric defect, as defined in the appended claims.

BRIEF DESCRIPTION OF THE DRAWINGS

For a better understanding of the present invention, some preferred embodiments will now be described, purely by way of non-limitative example, with reference to the accompanying drawings, in which.

DETAILED DESCRIPTION OF THE INVENTION

La present invention relates to the technical field of thermographic non-destructive inspection of a composite material structure, defined between a top surface and a bottom surface, to detect and measure at least a volumetric defect that extends from the top surface towards the bottom surface without necessarily reaching it. The above-mentioned volumetric defect is also known as a "resin pocket", and has a significant spatial extension in three dimensions defined by Cartesian axes X (length), Y (width) and Z (depth).

Figure 1:
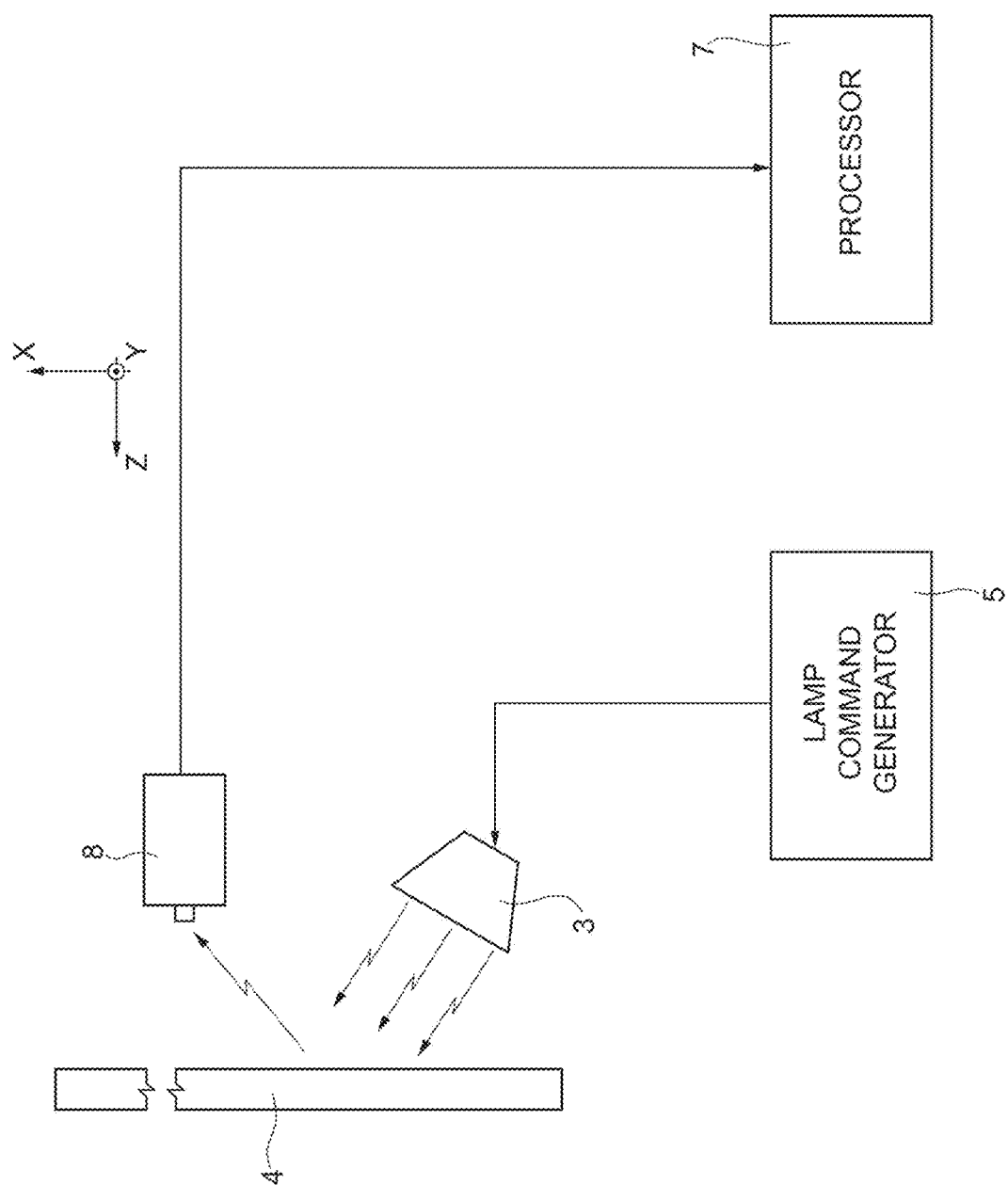
FIG. 1 schematically shows a thermographic inspection system.

In this context, width and length identify the dimensions of the defect that extend along directions Y and X, respectively, these directions being mutually orthogonal but lying parallel to the incidence surface (XY plane) of the modulated thermal wave emitted by the halogen lamp(s) 3 onto the item 4 (see FIG. 1). The width along Y of the defect has a value less than the length along X. Instead, the depth of the defect along Z identifies an extension of the defect along direction Z, orthogonal to both direction X and Y, and measured from the incidence surface towards the bottom surface of the item 4, the bottom surface being opposite to the incidence surface along Z.

Defects of the "vertical crack" type are usually considered two-dimensional or planar, as they extend mainly along two dimensions (depth along direction Z and length along a direction X), without showing a significant width (along direction Y). In other words, the extension of the defect along Y is much smaller than the respective extensions along X and Z and is typically less than 1/10 with respect to the smallest of the extensions along X and along Z. Defects of the "vertical crack" type can be thermally detected by using a non-uniform heat source or using the method described in WO 2014/044986, based on aspects that are not part of this disclosure and that, nevertheless, would not allow acquiring depth, width and length information. (i.e. in three dimensions) of volumetric defects, such as resin pockets in composite material structures.

Vertical planar defects, or "vertical cracks", might be detectable, but are not characterizable by the method according to the present invention. Contrariwise, according to one embodiment, the present invention provides for the use of a uniform heat source (e.g., halogen lamp) to detect volumetric defects. A defect can be defined volumetric, for the purposes of the present invention, when the ratio between the width along Y and the minimum extension between the depth along Z and the length along X is greater than 1/10.

Thus, reference will be made in the following to so-called "volumetric" defects (e.g., resin pockets), distinguishing them from so-called "planar" defects (e.g., vertical cracks). The distinction between planar defect and volumetric defect is, in any case, well known in the present invention's technical field of reference (non-destructive tests or inspections).

According to the present invention, a lock-in thermography system of the type shown in FIG. 1 is provided, and therefore will not be further described (common elements are hereinafter indicated with the same reference numerals). According to one aspect of the present invention, the signal generator 5 controls operation of the halogen lamp 3 via a periodic control signal, for example of the square or triangular or sawtooth waveform type, having, for example, a period of between 10 and 60 seconds, in particular equal to 25 s and a duty cycle of between 40 and 60%, in particular equal to 50%. In general, for the purposes of the present invention, the periodic control signal can be developed in a Fourier series. However, a purely sinusoidal control signal cannot be used according to the present invention. The "high" value of the control signal determines the time duration for which the halogen lamp 3 is switched on, while the "low" value of the control signal determines the time duration for which the halogen lamp 3 is switched off.

The thermal signal emitted from the item 4 is acquired over the entire operational time interval necessary for obtaining an adequate number of thermal cycles (for example three). Information related to the amplitude of the acquired thermal signal is not relevant for the purposes of the present invention. Phase information is used instead. The phase information of the received signal represents the difference, in terms of phase shift (measured in degrees), between the thermal signal emitted from the defect-free regions of the item 4 and the regions of the item 4 with defects.

The thermal signal captured by the thermographic camera 8 is, as stated above, sent to the computer 7. The signal sent from the thermographic camera 8 to the computer 7 is a thermal map of the item 4. This thermal map is representative of the different heat diffusive behaviour of regions, superficial and internal, of the item 4; the difference in heat flow with respect to a definitely defect-free zone is indicative of lack of homogeneity inside the item 4, such as to presume the presence of defects, in particular defects in the form of resin pockets that part from the surface of the item 4 and extend towards the inside of the item 4. The signal generated by the thermographic camera 8 is processed by the computer 7 to extract information related to the first and third harmonics of the signal. This processing can be performed, for example, via a series development of the received signal, for example by performing a Fourier transform on the thermal signal over time for each individual pixel or using other algorithms suitable for extracting this information.

As better described hereinafter, data analysis of the first harmonic enables determining the width L of any defects detected and, in certain conditions, also the depth. However, a better estimate of the depth of any defects detected can be obtained through joint analysis of the data of the first and third harmonics.

Figure 2:
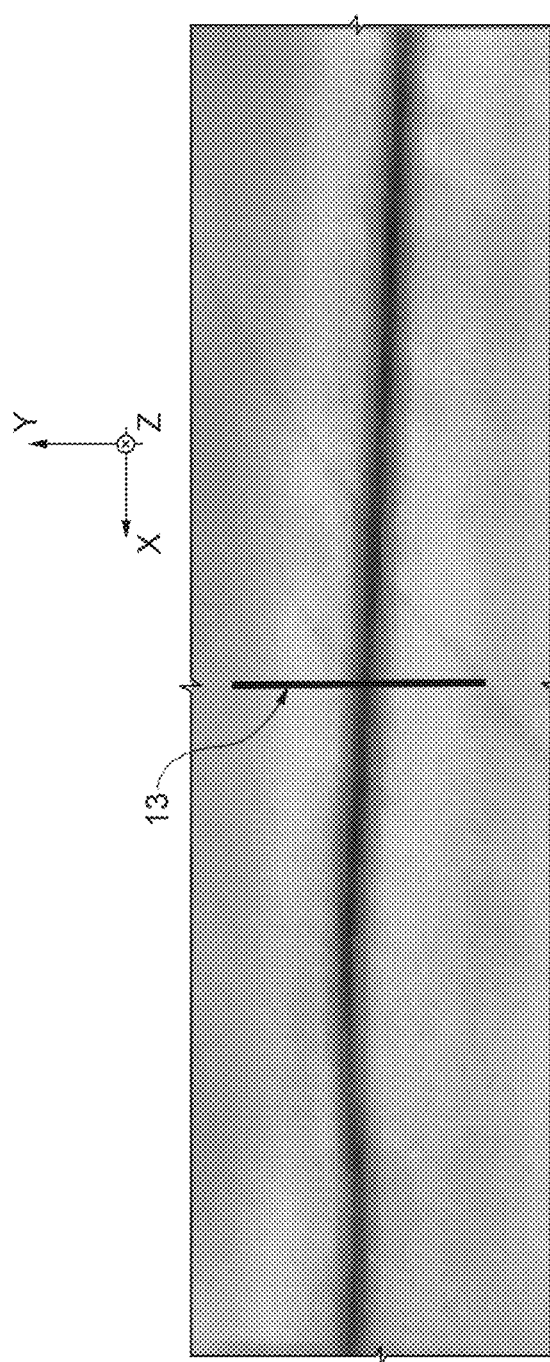
FIG. 2 shows a thermal image obtained by extraction from the processing of a thermal map generated by the system in FIG. 1, where the presence of a defect with an elongated shape may be noted.

As mentioned, information on the first harmonic is used for estimating the width L of the defect. FIG. 2 shows, by way of example, a thermal image of a portion of the item 4 processed so as to graphically represent in greyscale) the first harmonic of the thermal signal detected by the thermographic camera 8. In the representation used in FIG. 2, the darker regions are related to high phase difference values (modulus), while the lighter regions identify a small phase difference (modulus). The darker regions are associated with an imperfection or defect of the portion of the analysed item 4 (high phase difference).

The signal related to the first harmonic can be filtered beforehand, for example with a moving average filter, in order to reduce noise.

Figure 3A:
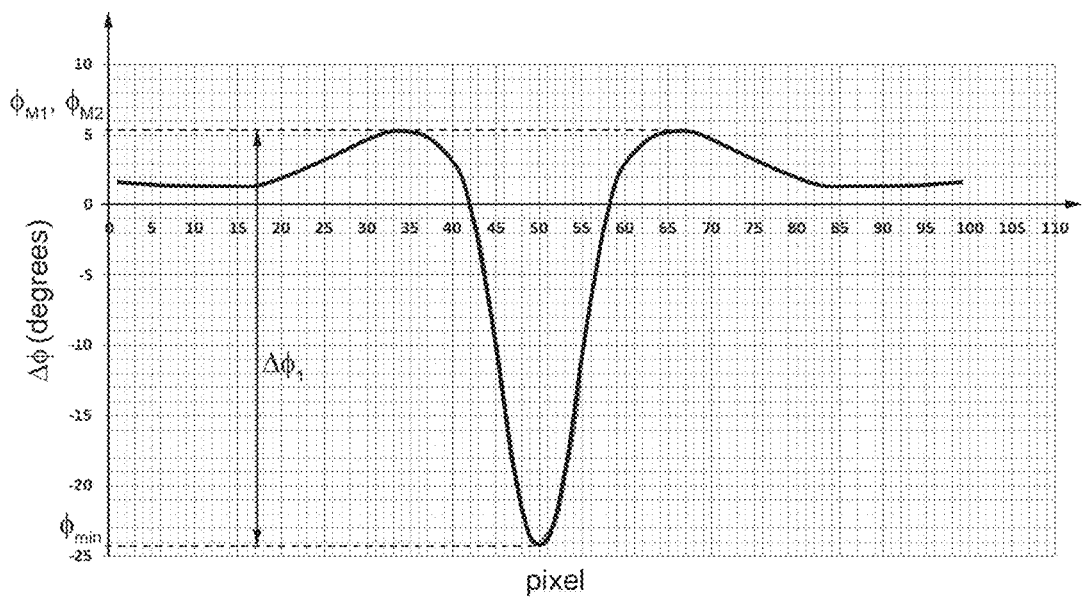
FIG. 3A represents the phase difference trend along survey line shown in FIG. 2, in an ideal case with no noise on the image of FIG. 2.

FIG. 3A shows a signal $S_{AP}$ that represents the phase difference trend along the survey line indicated by reference numeral 13 in FIG. 2. The phase trend is monitored along a plurality of survey lines, parallel to survey line 13. For example, it is possible to detect the phase difference trend along a plurality of survey lines 13 adjacent to one another (in terms of pixels), by analysing all of FIG. 2, or along survey lines separated from each other by a predefined distance (for example, separated from each other by a few pixels).

The signals thus obtained (similar to signal $S_{AP}$ in FIG. 3A) are processed individually in order to perform respective differential operations on these signals, generating respective derivative signals.

Figure 4:
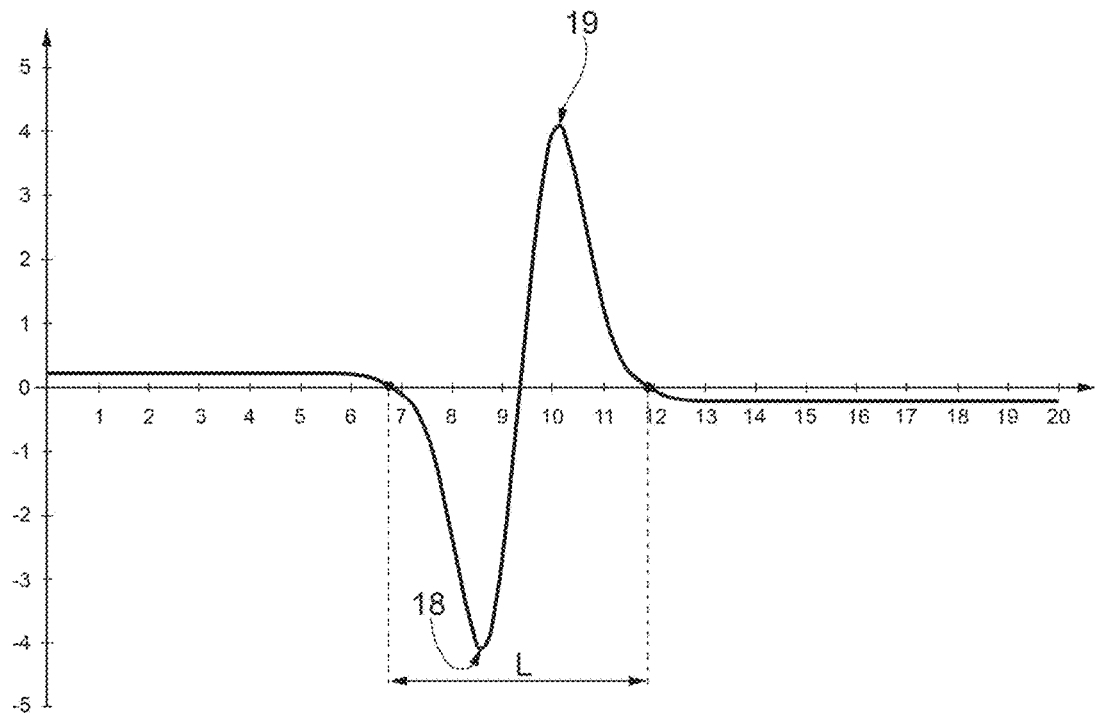
FIG. 4 shows the first derivative of the signal in FIG. 3A.

FIG. 4 shows the first derivate of the signal in FIG. 3A (derivative signal $S_{DER}$). The values obtained by means of differential operations are shown on the ordinate axis, while values indicative of the position along the survey line considered (in this case, along survey line 13) are shown on the abscissa axis. Through analysis of the derivative signal $S_{DER}$ in FIG. 4, it is possible to identify the width of the defect under analysis by measuring the distance L as the distance between the zero crossing immediately preceding the minimum point 18 and the zero crossing immediately following the maximum point 19. Alternatively, it is possible to use a value of zero or in the neighbourhood of zero as a threshold.

Figure 5:
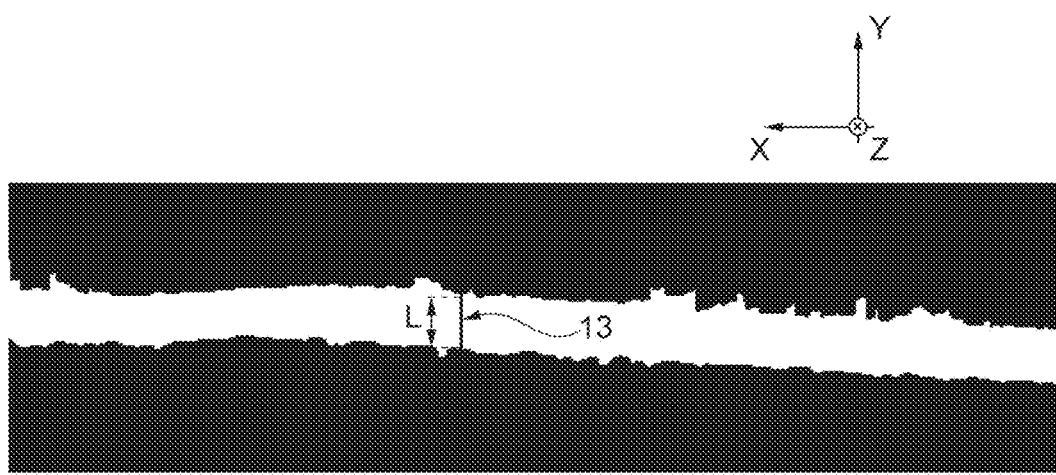
FIG. 5 shows the width trend of the defect in FIG. 2 obtained on the basis of the first derivate in FIG. 4.

By performing this operation for all the signals corresponding to the survey lines considered, a plurality of width L values of the analysed defect are obtained, which can be used to (graphically) construct the monochrome image in FIG. 5. The set of width L values calculated in this way is indicative of the variation in width of the defect under analysis, along an extension length of the defect.

In FIG. 5, each pixel belonging to a respective survey line, parallel to survey line 13 in FIG. 2, is coloured white in the region between the zero crossings of the respective derivative signal (region of width L in FIG. 4), and coloured grey outside of this region. The image in FIG. 5 is thus obtained, which shows the width, and its variation along the length, of the defect.

Calculation of the depth of the defect under consideration is then commenced.

The depth calculation operations are performed along respective survey lines of the thermal map, so as to cover the entire extension of the defect considered, similarly to that previously described for calculating the width of the defect.

In order to calculate the depth of the defect, first of all the signal $S_{AP}$ in FIG. 3A, related to the first harmonic, is considered. On the basis of this signal $S_{AP}$, the maximum values reached by signal $S_{AP}$ (values $\Phi_{M1}$ and $\Phi_{M2}$, equal to each other in the figure), and the minimum value reached by signal $S_{AP}$ (value $\Phi_{min}$ in the figure) are identified. The maximum values $\Phi_{M1}$ and $\Phi_{M2}$ are the maximum value of signal $S_{AP}$ that precedes the minimum value $\Phi_{min}$, and the maximum value of signal $S_{AP}$ that follows the minimum value $\Phi_{min}$, respectively. The parameter $\Delta\Phi_1$ is then obtained by calculating the excursion between ($\Phi_{min}$ and $\Phi_{M1}$ (or $\Phi_{M2}$), i.e. $\Delta\Phi_1=\Phi_{min}-\Phi_{M1}$.

Since, in a real case, the values $\Phi_{M1}$ and $\Phi_{M2}$ are not normally the same, it is advisable to calculate parameter $\Delta\Phi_1$ according to the formula:

$$\Delta\phi_1 = \phi_{min} - \frac{\phi_{M1} + \phi_{M2}}{2}$$

The operations discussed above for calculating $\Delta\Phi_1$ are performed in a similar manner on the signal related to the third harmonic of the signal generated by the thermographic camera 8, considered along survey line 13. The trend of the signal related to the third harmonic is not shown in the figures, but is similar to the trend of signal $S_{AP}$ in FIG. 3A, and exhibits two maximum points ($\Phi_{M1}'$ and $\Phi_{M2}'$) immediately preceding and following a minimum point $\Phi_{min}'$. By following the same steps, a phase difference value $\Delta\Phi_2$ is calculated according to the following formula:

$$\Delta\phi_2 = \phi'_{min} - \frac{\phi'_{M1} + \phi'_{M2}}{2}$$

Furthermore, for calculating $\Delta\Phi_1$ and $\Delta\Phi_2$, the operations discussed above are performed for a plurality of survey lines considered, in order to estimate the spatial development of the defect.

Figure 3B:
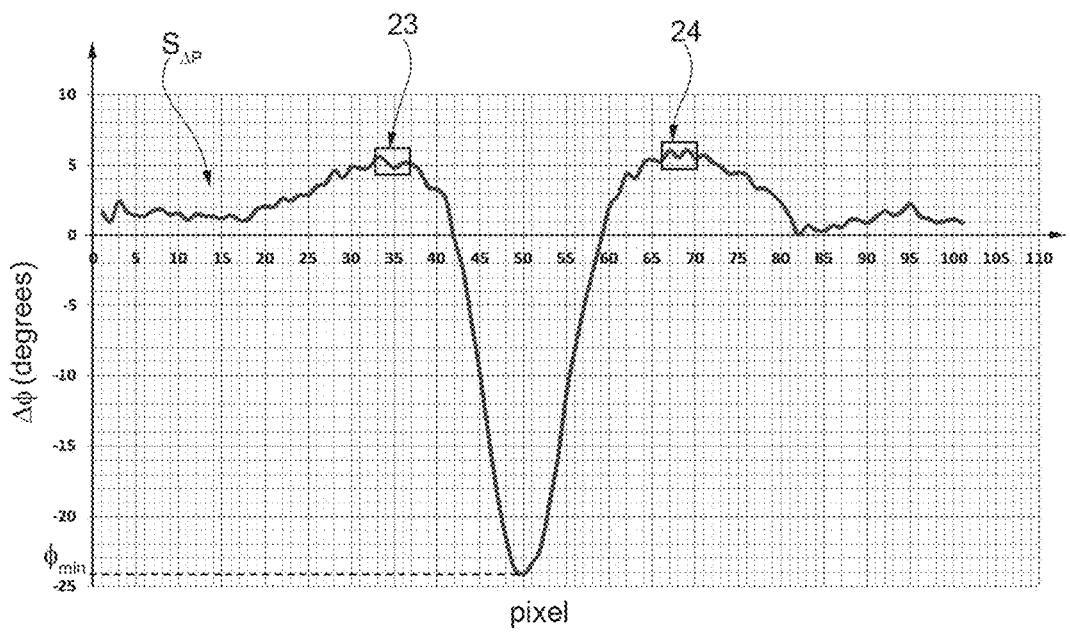
FIG. 3B represents the phase difference trend along a survey line shown in FIG. 2, in a real case with noise on the image of FIG. 2.

The applicant has found that, in practice, the signal $S_{\Delta P}$ related to the first harmonic is a highly variable signal, of the type shown in FIG. 3B. Therefore, the choice of precise maximum values $\Phi_{M1}$ and $\Phi_{M2}$ cannot give precise results. The same observations are also applicable to the signal related to the third harmonic.

In this case, the point value $\Phi_{M1}$ is replaced by the average value that signal $S_{\Delta P}$ assumes prior to the start of the "drop" to the minimum value $\Phi_{min}$, and the point value $\Phi_{M2}$ is replaced by the average value that signal $S_{\Delta P}$ assumes following, the end of the "rise" from the minimum value $\Phi_{min}$. To this end, a first plurality 23 of pixels is identified that precedes the start of slope inversion of signal $S_{\Delta P}$ (for example, a number of pixels ranging between 2 and 10, for example 5 pixels immediately preceding the slope inversion that identifies the beginning of the defect). A respective phase value (as identified on the ordinate axis) is assigned to each pixel of the first plurality 23 of pixels, and the average value $\Phi_{avg1}$ of the thus obtained phase values is then calculated. Then, always on the basis of signal $S_{\Delta P}$, a second plurality 24 of pixels is identified that follows the end of the slope inversion of the signal $S_{\Delta P}$ identifying the end of the defect considered (for example, a number of pixels ranging between 2 and 10, for example 5 pixels immediately following the slope inversion that identifies the end of the defect). A respective phase value (as identified on the ordinate axis) is assigned to each pixel of the second plurality 24 of pixels, and the average value $\Phi_{avg2}$ of the thus obtained phase values is then calculated.

The phase difference value $\Delta\Phi_1$ is then calculated according to the following formula:

$$\Delta\phi_1 = \phi_{min} - \frac{\phi_{avg1} + \phi_{avg2}}{2}$$

where $\Phi_{avg1}$ and $\Phi_{avg2}$ are calculated as previously described and $\Phi_{min}$ is the minimum phase value assumed by signal $S_{\Delta P}$.

For calculation of $\Delta\Phi_1$, the operations discussed above are performed in a similar manner on the signal related to the third harmonic of the signal detected (measured) by the thermographic camera 8, considered along survey line 13. Following the same steps, the phase difference value $\Delta\Phi_2$ is calculated according to the following formula:

$$\Delta\phi_2 = \phi'_{min} - \frac{\phi'_{avg1} + \phi'_{avg2}}{2}$$

where $\Phi'_{avg1}$ and $\Phi'_{avg2}$ are average values calculated in a similar manner to that previously described for calculating the average values $\Phi_{avg1}$ and $\Phi_{avg2}$, respectively, while $\Phi'_{min}$ is the minimum phase value assumed by the phase change signal related to the third harmonic.

The applicant has verified, by means of experimental testing, that the phase difference values $\Delta\Phi_1$ and $\Delta\Phi_2$ (parameters typically provided by known systems of lock-in thermography) are more correctly correlatable to the volume of the defect (resin pocket) instead of to its depth.

According to one aspect of the present invention, the depth p of the defect considered is calculated as a function of the values previously calculated of length L, phase difference $\Delta\Phi_1$ related to the first harmonic, and phase difference $\Delta\Phi_2$ related to the third harmonic. Therefore, also in this case, calculation of the depth is performed for each survey line considered. To acquire information on the variation in depth along the entire length of the defect considered, it is therefore necessary to calculate the depth value p for a plurality of survey lines parallel to each other.

Therefore, an estimate $p_E$ of the depth (considering only the first harmonic) is given by the following formula:

$$p_E = \Delta\Phi_1 \cdot (L+L_0)^{e1}$$

where L is the width of the defect, obtained as previously described on the survey line along which it wished to calculate the depth, $L_0$ is a correction parameter determined empirically as described below, for example with a value equal to $-0.1$, and $e_1$ is an empirically determined correction parameter, for example with a value equal to $-1$, which links the depth, width and phase difference together.

Figure 6:
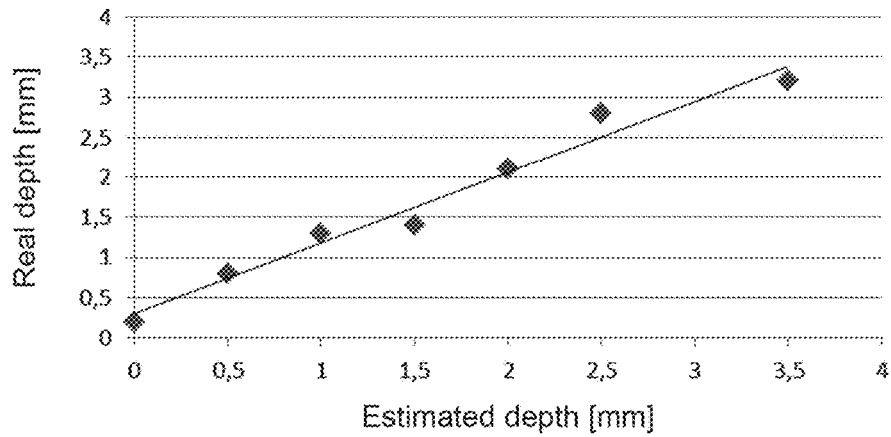
FIG. 6 shows a calibration curve, used for calculating a depth of the defect in FIG. 2.

A practicable calibration curve is obtained by comparing the estimated value $p_E$ of a plurality of reference samples (each having a defect of different depth) with a real depth value $p_{opt}$, obtained by direct measurement (e.g., optical) with destructive analysis of the respective reference sample. Note FIG. 6, where estimated values $p_E$ of the respective reference samples are shown on the abscissa axis and the measured values $p_{opt}$ are shown on the ordinate axis. Each point identified in the reference system in FIG. 6 represents a pair ($p_E$, $p_{opt}$) related to a reference sample. Interpolating these points with a linear function gives a straight line of the type $p_{opt} = m \cdot p_E + q$, where m is the angular coefficient and q is the intercept of the drawn line. Substituting the equation $p_E = \Delta\Phi_1 \cdot (L+L_0)^{e1}$ into the equation of the thus obtained line results in a first estimate of the depth measurement of the defect considered, obtained according to an aspect of the present invention, that is given by:

$$P_1 = m_1 \cdot (-\Delta\Phi_1) \cdot (L+L_0)^{e1} + q_1.$$

Performing the same operations for the third harmonic, results in a second estimate of the depth measurement of the defect considered, obtained according to an aspect of the present invention, that is given by:

$$P_2 = m_2 \cdot (-\Delta\Phi_2) \cdot (L+L_0)^{e1} + q_2.$$

In the case of defects in the form of resin pockets in composite material structures such as carton fibre, the applicant has verified that, for the material and the component subjected to the case study, the values of the parameters can be obtained in ranges such as, for example: $m_1$ in the range between 0.85 and 0.95 (and, in particular, the value $m_1 = 0.89$); $q_1$ in the range between $-0.4$ and $-0.8$ (and, in particular, the value $q_1 = -0.62$); $m_2$ in the range between 0.78 and 0.85 (and, in particular, the value $m_2 = 0.81$); and $q_2$ in the range between $-1.0$ and $-1.8$ (and, in particular, the value $q_2 = -1.5$).

The values obtained for $P_1$ and $P_2$ represent estimates of the depth of the defect, along the survey line considered.

Figure 7:
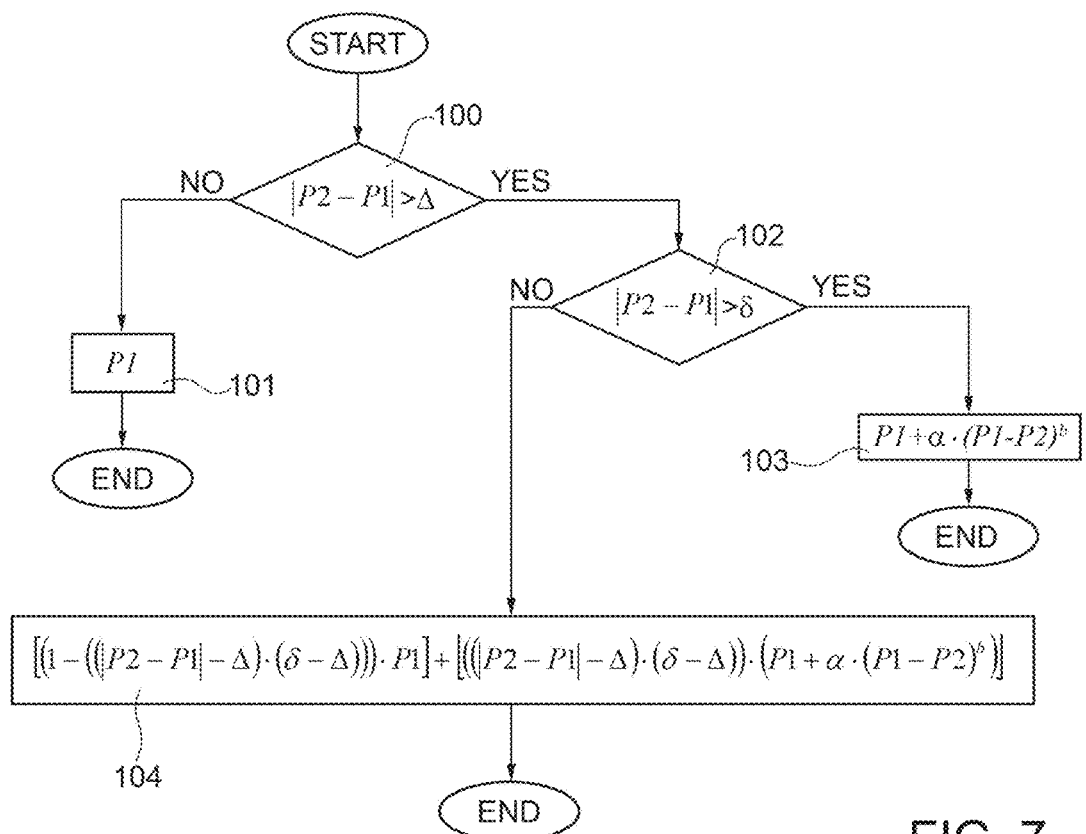
FIG. 7 shows, by means of a flowchart, the steps of calculating the depth of the defect shown in FIG. 2.

Then, with reference to the flowchart in FIG. 7, calculation of the depth of the defect is carried out.

First of all, step 100, it is checked if $|P_2 - P_1| > \Delta$, where $\Delta$ is equal to a very small value, and in any case not greater than a freely chosen and predefined measurement uncertainty value (in the case study, for example, a value of 0.2 mm was chosen for the measurement uncertainty, and so the value for $\Delta$ was chosen to be below the measurement uncertainty by several orders of magnitude, between 0.00005 mm and 0.0005 mm, in particular equal to 0.0001 mm). The value of $\Delta$ can also be chosen equal to zero. In general, step 100 has the function of checking if the depth values obtained using the first and the third harmonic are substantially equal to each other. In this condition, it is unnecessary to proceed any further and the depth value of the defect considered is given by the value of $P_1$ (NO exit from step 100, and execution of step 101).

Otherwise, YES exit from step 100, processing passes to step 102, where it is checked if $|P_2-P_1|>\delta$, where $\delta$ has a value greater than $\Delta$ and less than twice the measurement uncertainty (in the case study, the value of $\delta$ is, for example, comprised between 0.0005 and 0.002 mm, in particular equal to 0.001 mm). In general, step 102 has the function of checking if the depth values obtained using the first and the third harmonic are very similar to each other, even if not being identical.

If positive, YES exit from step 102, processing passes to step 103, where the depth value of the defect considered is defined according to the formula:

$$P_1+\alpha \cdot (P_1-P_2)^b,$$

where $\alpha$ is a constant chosen in the range 0.08-0.15, for example equal to 0.1, and b is a constant chosen in the range 1-1.5, for example equal to 1.

The constants a and b are constants obtained empirically by means of a calibration process described below. In the event of the NO exit from step 102, processing passes to step 104, where the depth value of the defect considered is calculated according to the formula:

$$[(1-((|P2-P1|-\Delta)\cdot(\delta-\Delta)))\cdot P1\;]+[((|P2-P1|-\Delta)\cdot(\delta-\Delta))\cdot (P1+\alpha\cdot(P1-P2)^b)]$$

The values of parameters $\alpha$, $\Delta$, $\delta$ and b can be different from that indicated, especially in the case of materials or manufacturing processes different from that of the case study. In general, the rule is that the above-mentioned parameters are chosen such that, in the various conditions assumed in steps 100 and 102, the error between the calculated depth value and the real depth value, measured on test samples by means of destructive methods, is minimized. In this phase, given the small number of parameters to be set, it is possible to proceed by means of a trial and error approach, for example, of an automatic (computerized) type.

It is obvious from what has been described that, given the possibility of significantly reducing the uncertainty in the quantification of the width and depth values of a defect such as a resin pocket, the method according to the present invention represents a significant development with respect to that reported in the literature and known in the state of the art.

Finally, it is clear that modifications and variants can be made to the invention described and illustrated herein without departing from the scope of the present invention, as defined in the appended claims.

The invention claimed is:

1. A thermographic non-destructive inspection method of a composite material structure, including an incidence surface and a bottom surface arranged at a distance from the incidence surface for detecting and measuring at least one volumetric defect that extends from the incidence surface towards the bottom surface, comprising the acts of:
   a'—controlling on and off states of a halogen lamp via a periodic non-sinusoidal control signal having a period of between 10 and 60 seconds and a duty cycle of between 40 and 60%, thus generating a periodic non-sinusoidal modulated thermal wave;
   a"—applying the periodic non-sinusoidal modulated thermal wave to the incidence surface;
   b'—capturing, by a thermographic camera, a return thermal wave emitted from the structure in response to the periodic non-sinusoidal modulated thermal wave applied;
   b"—generating, by the thermographic camera, a temperature signal forming a thermal map of the composite material structure housing the volumetric defect and identifying a phase shift between the modulated thermal wave and a return thermal wave emitted from the structure in response to the modulated thermal wave;
   b'"—sending, by the thermographic camera, the temperature signal to a processor;
   c—processing, by the processor, the temperature signal to obtain a first sub-signal related to the phase of the first harmonic of the temperature signal;
   d—identifying, by the processor, a first dimension (L) of said defect as a function of the phase of the first harmonic of the temperature signal;
   e—computing, by the processor, a first intermediate parameter ($\Delta\Phi_1$) by calculating the difference, in degrees, between a minimum value and a maximum value, or between a minimum value and a mean value of a plurality of values in a range around the maximum value, of the first sub-signal;
   f—processing, by the processor, the temperature signal to obtain a second sub-signal related to the phase of the third harmonic of the temperature signal;
   g—calculating, by the processor, a second intermediate parameter ($\Delta\Phi_2$) as the difference, in degrees, between a minimum value and a maximum value, or mean of a plurality of values in a range around the maximum value, of the second sub-signal; and
   h—identifying, by the processor, a second dimension of the defect as a function of the first dimension (L), the first intermediate parameter ($\Delta\Phi_1$) and the second intermediate parameter ($\Delta\Phi_2$).

2. The method according to claim 1, wherein the act of identifying the first dimension (L) comprises:
   calculating, by the processor, the first derivative of the sub-signal related to the phase of the first harmonic;
   identifying, by the processor, a first intersection point between said first derivative and a threshold value immediately following a maximum value of the first derivative, and a second intersection point between said first derivative and the threshold value immediately preceding a minimum value of the first derivative; and
   identifying, by the processor, the first dimension (L) of said defect as a function of the distance between said first and said second intersection point.

3. The method according to claim 1,
   further including defining a plurality of survey lines in a region of said thermal map including the defect, said survey lines extending parallel to one another along the first dimension, of said defect, to be calculated,
   and wherein the acts from c- to f- are performed for each survey line.

4. The method according to claim 1, identifying the second dimension (P1) comprises:
   calculating, by the processor, a first estimate of depth, P1, of the defect as a function of the first intermediate parameter ($\Delta\Phi_1$), according to the formula $$P1=m_1\cdot(-\Delta\Phi_1\cdot(L+L_0)^{e1})+q_1,$$

where $m_1$ is the angular coefficient of a first linear approximation of a succession of points obtained from the comparison between a real measurement of the second dimension on a test sample and an estimate of the second dimension on the test sample performed on the basis of the first sub-signal, $q_1$ is the intercept of said first linear approximation, $\Delta\Phi_1$ is said first intermediate parameter, L is the first dimension of the defect, and $L_0=-0.1$ and $e_1=-1$ are correction factors; and associating, by the processor, the first estimate of depth P1 with the second dimension of the defect.

5. The method according to claim 4, wherein identifying the second dimension further comprises calculating a second estimate of depth, P2, of the defect as a function of the second intermediate parameter ($\Delta\Phi_2$), according to the formula $$P2=m_2 \cdot (-\Delta\Phi_2 \cdot (L+L_0)^{e1})+q_2,$$

where $m_2$ is the angular coefficient of a second linear approximation of a succession of points obtained from the comparison between a real measurement of the second dimension on a test sample and an estimate of the second dimension on the test sample performed on the basis of the second sub-signal, $q_2$ is the intercept of said second linear approximation, $\Delta\Phi_2$ is said second intermediate parameter, L is the first dimension of the defect, and $L_0=-0.1$ and $e_1=-1$ are correction factors; and identifying, by the processor, the second dimension of the defect as a function of the first estimate of depth P1 and of the second estimate of depth P2.

6. The method as claimed in claim 5, wherein identifying the second dimension of the defect as a function of the first estimate of depth P1 and of the second estimate of depth P2 comprises:
 i.—verifying, by the processor, if |P2-P1|>Δ, Δ being a value lower than a predefined measurement uncertainty value;
 ii.—if the act i. has a negative outcome, then setting, by the processor, the second dimension of the defect to the value of the first estimate of depth P1; otherwise:
 iii.—setting, by the processor, the second dimension of the defect to the value obtained according to the formula $P1+\alpha \cdot (P1-P2)^b$, where α and b are constants chosen so as to minimize the estimation error of the second dimension of the defect, where α is in the range 0.08-0.15 and b is in the range 1-1.5.

7. The method according to claim 6, further comprising, before act iii., verifying, by the processor, if |P2-P1|>δ, where δ is a value higher than Δ and lower than twice the measurement uncertainty value, and performing act iii. only if the act of verifying if |P2-P1|>δ has a positive outcome; otherwise: iv.—setting the second dimension of the defect to the value obtained according to the formula $$[(1-((|P2-P1|-\Delta)\cdot(\delta-\Delta)))\cdot P1]+[((|P2-P1|-\Delta)\cdot(\delta-\Delta))\cdot (P1+\alpha\cdot(P1-P2)^b)]$$

where α is in the range 0.08-0.15 and b is in the range 1-1.5.

8. A thermographic non-destructive inspection system of a composite material structure, including an incidence surface and a bottom surface arranged at a distance from the incidence surface for detecting at least a volumetric defect that extends from the incidence surface towards the bottom surface, comprising:
 a halogen lamp;
 a controller, adapted to generate a periodic non-sinusoidal control signal having a period of between 10 and 60 seconds and a duty cycle of between 40 and 60%, coupled to the halogen lamp to turn on and off the halogen lamp via the periodic non-sinusoidal control signal, thus generating a periodic non-sinusoidal modulated thermal wave,
 wherein the halogen lamp is operatively coupled to the incidence surface to apply the periodic non-sinusoidal modulated thermal wave to the incidence surface;
 a thermographic camera, configured to acquire a return thermal wave emitted from the structure in response to the periodic non-sinusoidal modulated thermal wave; generate a temperature signal forming a thermal map of the composite material structure housing the volumetric defect and identifying a phase shift between the modulated thermal wave and a return thermal wave emitted from the structure in response to the modulated thermal wave; and output the temperature signal; and
 a processor, operatively coupled to the thermographic camera, configured to:
 a.—receive acquire the temperature signal outputted from the thermographic camera and identify, based on said temperature signal, a phase shift between the modulated thermal wave and the return thermal wave;
 b.—process the temperature signal to generate a first sub-signal related to the phase of the first harmonic of the temperature signal;
 c.—calculate the first derivative of the first sub-signal related to the phase of the first harmonic;
 d.—identify a first dimension (L) of said defect as a function of the first harmonic of the temperature signal;
 e—calculate a first intermediate parameter ($\Delta\Phi_1$) by calculating the amplitude, in degrees, between a minimum value and a maximum value, or between a minimum value and a mean value of a plurality of values in a range around the maximum value, of the first sub-signal,
 processor being further configured to:
 f—process the temperature signal to obtain a second sub-signal related to the phase of the third harmonic of the temperature signal;
 g—calculate a second intermediate parameter ($\Delta\Phi_2$) by calculating the difference, in degrees, between a minimum value and a maximum value, or mean of a plurality of values in a range around the maximum value, of the second sub-signal; and
 h—identify the second dimension (P1) of the defect as a function of the first dimension (L), of the first intermediate parameter ($\Delta\Phi_1$) and of the second intermediate parameter ($\Delta\Phi_2$).

9. The system according to claim 8, wherein, the first dimension and the second dimension of said volumetric defect are coplanar with the incidence surface and are such that the first dimension is less than the second dimension, the volumetric defect further including a depth extending orthogonally to the first and to the second dimension, wherein the ratio between the first dimension and the lesser value of the depth and the second dimension is greater than 1/10.

10. The system according to claim 8, wherein, to identify the first dimension (L), the the processor is further configured to:
 identify a first intersection point between said first derivative and a threshold value immediately following a maximum value of the first derivative, and a second intersection point between said first derivative and the threshold value immediately preceding a minimum value of the first derivative; and
 identify the first dimension (L) of said defect as a function of the distance between said first and said second intersection point.

11. The system according to claim 10, wherein the processor is further configured to calculate a second estimate of depth, P2, of the defect as a function of the second intermediate parameter ($\Delta\Phi_2$), according to the formula $$P2 = m_2 \cdot (-\Delta\Phi_2 \cdot (L+L_0)^{e1}) + q_2,$$

where $m_2$ is the angular coefficient of a second linear approximation of a succession of points obtained from the comparison between a real measurement of the second dimension on a test sample and an estimate of the second dimension on the test sample performed on the basis of the second sub-signal, $q_2$ is the intercept of said second linear approximation, $\Delta\Phi_2$ is said second intermediate parameter, L is the first dimension of the defect, and $L_0=-0.1$ and $e_1=-1$ are correction factors; and identify the second dimension of the defect as a function of the first estimate of depth P1 and of the second estimate of depth P2.

12. The system according to claim 11, wherein the processor is further configured to identify the second dimension of the defect as a function of the first estimate of depth P1 and of the second estimate of depth P2 by performing the sub-acts of:

i.—verifying if |P2-P1|>$\Delta$, where $\Delta$ is a value lower than a predefined measurement uncertainty value;

ii.—if the sub-act i. has a negative outcome, then setting the second dimension of the defect to the value of the first estimate of depth P1; otherwise:

iii.—setting the second dimension of the defect to the value obtained according to the formula $P1+\alpha \cdot (P1-P2)^b$, where $\alpha$ and b are constants chosen so as to minimise the estimation error of the second dimension of the defect, where $\alpha$ is in the range 0.08-0.15 and b is in the range 1-1.5.

13. The system according to claim 12, wherein the processor is further configured, prior to act iii., to verify if |P2-P1|>$\delta$, where $\delta$ is a value higher than $\Delta$ and lower than twice the measurement uncertainty value, and perform act iii. only if the act of verifying if |P2-P1|>$\delta$ has a positive outcome; otherwise:

iv.—setting the second dimension of the defect to the value obtained according to the formula $$[(1-(( |P2-P1|-\Delta)\cdot(\delta-\Delta)))\cdot P1] - [(( |P2-P1|-\Delta)\cdot(\delta-\Delta))\cdot (P1+\alpha\cdot(P1-P2)^b)]$$

where $\alpha$ is in the range 0.08-0.15 and b is in the range 1-1.5.

14. The system according to claim 8, wherein the act of generating a temperature signal includes generating a thermal map of at least one portion of the structure including the defect, said processor being further configured to:

define a plurality of survey lines in a region of said thermal map including the defect, said survey lines extending parallel to one another along the first dimension, of said defect, to be calculated; and perform the acts b. -h. for each survey line.

15. The system according to claim 14, wherein the processor is further configured to:

calculate, for each survey line, a first estimate of depth, P1, of the defect as a function of the first intermediate parameter ($\Delta\Phi_1$), according to the formula $$P1 = m_1 \cdot (-\Delta\Phi_1 \cdot (L+L_0)^{e1}) + q_1,$$

where $m_1$ is the angular coefficient of a first linear approximation of a succession of points obtained from the comparison between a real measurement of the second dimension on a test sample and an estimate of the second dimension on the test sample performed on the basis of the first sub-signal, $q_1$ is the intercept of said first linear approximation, $\Delta\Phi_1$ is said first intermediate parameter, L is the first dimension of the defect, and $L_0=-0.1$ and $e_1=-1$ are correction factors; and associate the first estimate of depth P1 with the second dimension of the defect.

16. The system according to claim 8, wherein said composite material of the structure is carbon fiber and said volumetric defect is a resin pocket.

* * * * *

UNITED STATES PATENT AND TRADEMARK OFFICE
CERTIFICATE OF CORRECTION

PATENT NO. : 10,444,173 B2
APPLICATION NO. : 15/216221
DATED : October 15, 2019
INVENTOR(S) : Giacomo Maione et al.

It is certified that error appears in the above-identified patent and that said Letters Patent is hereby corrected as shown below:

In the Specification

Column 2, Line 48: Delete "equal to 2nf" and insert --equal to $2\pi f$-- therefor.

Column 3, Lines 44-45: Delete "along survey line" and insert --along a survey line-- therefor.

Column 4, Line 28: Delete "information. (i.e. in" and insert --information (i.e. in-- therefor.

Column 5, Line 37: Delete "represent in greyscale)" and insert --represent (in greyscale)-- therefor.

Column 6, Line 38: Delete "between (Φmin" and insert --between Φmin-- therefor.

Column 7, Line 11: Delete "following, the end" and insert --following the end-- therefor.

Column 9, Line 18: Delete "where αis" and insert --where α is-- therefor.

Column 9, Line 21: Delete "The constants a" and insert --The constants α-- therefor.

In the Claims

Claim 8, Column 12, Line 15: Delete "receive acquire the temperature" and insert --acquire the temperature-- therefor.

Claim 13, Column 13, Line 36: Delete "|P2-P1| >67" and insert --|P2-P1| >δ-- therefor.

Claim 13, Column 14, Line 4: Delete "P1] – [(((|P2-P1|" and insert --P1] + [(((|P2-P1|-- therefor.

Signed and Sealed this
Twelfth Day of May, 2020

Andrei Iancu
*Director of the United States Patent and Trademark Office*